US008801767B2

(12) United States Patent
Roy

(10) Patent No.: US 8,801,767 B2
(45) Date of Patent: Aug. 12, 2014

(54) DRUG ELUTING STENT AND A GUIDE CATHETER DEVICE ASSEMBLY FOR IMPLANTING THE SAME

(76) Inventor: Vipul Narain Roy, New Delhi (IN)

( * ) Notice: Subject to any disclaimer, the term of this patent is extended or adjusted under 35 U.S.C. 154(b) by 701 days.

(21) Appl. No.: 13/108,254

(22) Filed: May 16, 2011

(65) Prior Publication Data

US 2011/0218611 A1    Sep. 8, 2011

Related U.S. Application Data

(63) Continuation-in-part of application No. 10/628,207, filed on Jul. 29, 2003, now abandoned.

(51) Int. Cl.
*A61L 27/54* (2006.01)
(52) U.S. Cl.
USPC ........... 623/1.11; 606/194; 606/195; 606/198
(58) Field of Classification Search
USPC ................. 606/191, 192, 193, 194, 195, 198; 623/1.11, 1.12, 1.42

IPC ..................... A61L 27/54; A61F 2/84
See application file for complete search history.

(56) References Cited

U.S. PATENT DOCUMENTS

| | | | | |
|---|---|---|---|---|
| 5,776,099 A | * | 7/1998 | Tremulis | 604/96.01 |
| 6,077,273 A | | 6/2000 | Euteneuer et al. | |
| 6,589,271 B1 | * | 7/2003 | Tzeng et al. | 607/105 |
| 6,666,880 B1 | | 12/2003 | Chiu et al. | |
| 7,678,128 B2 | * | 3/2010 | Boyle et al. | 606/192 |
| 2003/0208222 A1 | | 11/2003 | Zadno Azizi | |

OTHER PUBLICATIONS

"USPTO Office Action", dated Oct. 17, 2006, Parent U.S. Appl. No. 10/628,207.

* cited by examiner

*Primary Examiner* — Vy Q Bui
(74) *Attorney, Agent, or Firm* — LeonardPatel PC

(57) ABSTRACT

The present invention relates to a drug eluting stent for delivering therapeutic agents to a body lumen. The stent includes an expandable substrate configured for implantation in a vessel of a human body and a therapeutic agent composition coated over the stent. The balloon catheter shaft has a resilient unit that helps to transmit a force to the distal end, thereby helping to cross lesions.

13 Claims, 16 Drawing Sheets

DRUG ELUTING STENT AND A GUIDE CATHETER DEVICE ASSEMBLY FOR IMPLANTING THE SAME

CROSS-REFERENCE TO RELATED APPLICATION

This application is a continuation-in-part application of U.S. application Ser. No. 10/628,207, filed on Jul. 29, 2003.

FIELD

The present invention relates to a drug eluting stent and a guide catheter device and, more specifically, to a drug eluting stent for delivering therapeutic agents to a body lumen and guide catheter device assembly for implanting the same.

BACKGROUND

Generally, drugs are given either orally or intravenously (IV). This is a systemic administration that distributes the drug all over the body, but requires a much larger dose. However, in local administration of drugs, the drug is delivered at the desired site, reducing the dose and the systemic side effects. With respect to cardiac problems, a drug can be mounted on a stent, balloon, a microcapsule, a special pellet, or any suitable local administration mechanism.

A stent is a medical device that is introduced to a body lumen. Typically, the stent is implanted in a blood vessel at the site of a stenosis or aneurysm endoluminally, i.e., by so-called "minimally invasive techniques." The stent in a radially reduced configuration, optionally restrained in a radially compressed configuration by a sheath and/or catheter, is delivered by a stent delivery system, "introducer", or a "catheter device" to the site where the stent is required. The introducer may enter the body from an access location outside of the body, such as through the patient's skin, or by a "cut down" technique in which the entry blood vessel is exposed by minor surgical means.

Stents and similar devices such as stent-grafts, expandable frameworks, and similar implantable medical devices, are radially expandable endoprostheses. These devices are typically intravascular implants capable of being implanted transluminally and enlarged radially after being introduced percutaneously. Stents can be implanted in a variety of body lumens or vessels such as within the vascular system, urinary tracts, bile ducts, fallopian tubes, coronary vessels, secondary vessels, etc. Stents may be self-expanding, expanded by an internal radial force, such as when mounted on a balloon, or expanded by a combination of self-expansion and balloon expansion (hybrid expandable).

The stent can be created by methods including cutting or etching a design from a tubular stock, from a flat sheet that is cut or etched and is subsequently rolled, or from one or more interwoven wires or braids.

To prevent thrombosis and restenosis, and to treat vasculature tissue, there is a need to provide therapeutic agents directly at the site of stent deployment. One approach is through the use of a medicated stent to reduce the major proportion of the dosage amount of a drug administered via IV or orally. However, scientists have been working to develop a release profile of the medicated stent so that a minimal amount of a drug is given to the patient and, at the same time, having enhanced efficacy to cure thrombosis and restenosis.

In the field of angioplasty a guide catheter system for guiding an angioplasty balloon catheter into a patient's arterial system is known. Angioplasty has gained wide acceptance in recent years as an efficient and effective method for treating certain types of vascular diseases. In particular, angioplasty is widely used for expanding a constricted area or stenosis in coronary arteries. It is also used for treatment of stenoses in other parts of the vascular system as well.

The most widely used form of angioplasty makes use of an angioplasty balloon catheter, which has an inflatable balloon at its distal end. Using fluoroscopy, the physician guides the angioplasty balloon catheter through the vascular system until the balloon is positioned across the stenosis. The balloon is then inflated by supplying fluid under pressure through an inflation lumen connected to the balloon. The inflation of the balloon imparts a stretching force to the stenosis and artery wall to re-establish an acceptable blood flow through the artery. An angioplasty balloon catheter is normally introduced and directed through a patient's vascular system by a guide catheter. Guide catheters generally comprise a stiff shaft to provide support for the angioplasty balloon catheter as it is advanced through a patient's vascular system. The dimension of the guide catheter generally coincides with the insertion artery of a patient, and is generally large enough so that the angioplasty balloon catheter may easily insert therethrough to the coronary ostium. However, the dimension of the guide catheter is generally larger than the smaller dimension coronary arteries of the heart and thus its insertion through these arteries is restricted. In addition, the guide catheter is too stiff to negotiate the tortuous path of the coronary arteries. Thus, when a stenosis is located within these smaller dimension arteries, it is difficult for the guide catheter to provide assistance directly thereto. In this regard, discussed below are some of the conventional stent delivery systems, or "introducers" or "catheter devices"

Extra-Support Guide Wire/Guide Catheter Or Both: The shaft of guide wire is stronger than a standard wire and requires more force to buckle. However, this causes a concertina effect in vasculature (because of its strength or rigidity the vessel course changes) creating problems and also more likely to cause dissection.

While the use of the extra guide wires provides more support, using the extra guide wires results in a larger guide catheter. In this situation, guiding to the parent vessel makes the procedure difficult, time consuming and may also cause extra blood loss. Puncture site problems are also increased due to the larger diameter guide catheter causing an increase in hematoma or pseudo-aneurysm. Also, stent deployment becomes more difficult as the extra guide wires have to be withdrawn.

Over The Wire Balloon: Using an over the wire balloon after the guide-wire has already crossed the lesion means using a doc/link or other guide wire lengthening device to switch to the over the wire balloon. However, such a technique creates difficulties of not using a rapid exchange balloon catheter.

Deep Throat Guide: In this technique, a guiding catheter is pushed inside the artery. This offers more length before the guide catheter is pushed far back in the aortic root. However, the deep throat guide is associated with dissection in the artery with issues of the left main, proximal left anterior descending (LAD) or left circumflex (LCx) or ostial/proximal right coronary artery (RCA) dissection and complications as described above. It is also associated with severe spasms of the proximal part of the artery.

Anchoring Balloon: In this technique, in another small artery, a separate wire and small balloon are inflated to act as an anchor. However, changing to a larger guide predisposes the patient to problems as described above in the extra guide wire section. This technique also causes restenosis in the anchored balloon segment of the artery and can also cause tearing or avulsion of this segment with disastrous consequences.

Undertreat: Sometimes in above situation a smaller diameter balloon is dilated initially. However, stent deployment is not possible at a later time and the lesion is therefore undertreated.

Rotablator: The steps to change to a large size guide catheter lead to the associated problems described above, and the chance of restenosis is increased greatly.

Certain guide catheters provide extra-support (e.g., amplatzer, etc.), because the curvature of the catheters is designed to make use of the opposite aortic wall. Thus, the catheters will require more force than standard guide catheters to be pushed back. However, these types of catheters are more difficult to maneuver in the aortic root and are more likely to injure proximal vessels (e.g., the left main or proximal RCA). This has serious consequences to the left main/proximal RCA dissection. For instance, it may result with stenting an unprotected left main and causing lifetime dual antiplatelet therapy, which have serious long-term consequences.

In addition, the main problems after percutaneous transluminal coronary angioplasty (PTCA) and stent implantation are:

Restenosis: The occurrence of restenosis causes loss of lumen and, thus, blocks the artery again. Restenosis is caused by smooth muscle cell hyperplasia and intracellular matrix.

Stent Thrombosis: This occurs due to the clot formation over the stent. This is rare as compared to restenosis but has sudden onset and presents an acute myocardial infarction (i.e., heart attack) and has devastating consequences. The clot has two principal components, fibrin meshwork and platelets.

Scientists and medical practitioners have observed that while the standard balloon catheter along with stent is placed in the coronary or peripheral artery by a conventional catheter delivery system, the following limitations can be encountered:

a) In case that there is an obstruction in the coronary or peripheral artery in its path, such obstruction restricts the movement of the catheter. In such situations, if the catheter is further pushed, the guide wire-balloon assembly will start curving down and finally the guide wire with the balloon will fall back as shown in FIGS. 1B and 1C.

b) In some situations, when the angioplasty is carried out, and balloon is being pulled back, firstly it is pushed and then pulled back sequentially. However, sometimes during pulling back, the balloon tends to get stuck and thus in the assembly the length of the balloon catheter is being reduced, to accommodate the reduced length of the balloon catheter, the guide catheter will be sucked inside the artery as shown in the FIGS. 1(D-E). This sucking of guide catheter can dissect distal left main and proximal LAD, which can in turn cause serious repercussions to the patient.

c) Often it is noticed that the stent comes out of the balloon and embolisms occur somewhere in the vascular bed.

SUMMARY

Certain embodiments of the present invention may provide solutions to the problems and needs in the art that have not yet been fully identified, appreciated, or solved by current stents and/or catheters.

One or more embodiments of the present invention pertain to a drug eluting stent and a guide catheter device assembly to be used during angioplasty for any artery or vein.

Some embodiments also pertain to improving the drug release profile of the therapeutic agent composition coated over the stent, as well as controlling the release of a quantity of the therapeutic agent composition in a desired manner.

In one embodiment of the present invention, a drug eluting stent is provided for delivering therapeutic agents to a body lumen. The drug eluting stent includes a stent having an expandable substrate configured to be implanted in a vessel of a human body. The drug eluting stent also includes a therapeutic agent composition coated over the stent, the therapeutic agent composition including anticoagulants, Platelet Glycoprotein IIb/IIIa Receptor Antagonists, and a cytostasis or cytotoxic agent. The proportion of anticoagulants, platelet glycoprotein IIb/IIIa receptor antagonists and the cytostasis or cytotoxic agent can have a range of 1:0.15:0.5 to 1:0.2:1, and the edges of the stent having a 3-30 times higher concentration of drugs as compared to the middle segment of the stent in order to obtain a desired release profile of the coated composition.

In another embodiment of the present invention, a guide catheter device assembly is provided for angioplasty. The assembly includes a guide catheter having a proximal end, a distal end, and an inflation lumen extending therethrough. A balloon catheter is placed inside the guide catheter, the balloon catheter having a proximal end, a distal end, a guide wire lumen and a balloon lumen. A fluid inflatable balloon is connected to the distal end of the balloon lumen. A guide wire is extended through the guide wire lumen of the balloon catheter. A drug eluting stent is mounted over the balloon in order to place the same at a desired location in the artery. A resilient unit is provided at a predetermined distance from the proximal end of the balloon catheter to absorb and transmit a required force in order to maintain the alignment of the guide catheter and the balloon catheter. The edges of the stent have a higher concentration of drugs as compared to the middle segment of the stent.

BRIEF DESCRIPTION OF THE DRAWINGS

For a proper understanding of the invention, reference should be made to the accompanying figures. These figures depict only some embodiments of the invention and do not limit the scope of the invention. Regarding the figures.

DETAILED DESCRIPTION OF THE EMBODIMENTS

It will be readily understood that the components of the invention, as generally described and illustrated in the figures herein, may be arranged and designed in a wide variety of different configurations. Thus, the following detailed description of the embodiments is not intended to limit the scope of the invention as claimed, but is merely representative of selected embodiments of the invention.

The features, structures, or characteristics of the invention described throughout this specification may be combined in any suitable manner in one or more embodiments. For example, the usage of "certain embodiments," "some embodiments," or other similar language, throughout this specification refers to the fact that a particular feature, structure, or characteristic described in connection with an embodiment may be included in at least one embodiment of the invention. Thus, appearances of the phrases "in certain embodiments," "in some embodiments," "in other embodiments," or other similar language, throughout this specification do not necessarily all refer to the same embodiment or group of embodiments, and the described features, structures, or characteristics may be combined in any suitable manner in one or more embodiments.

Figure 1A:
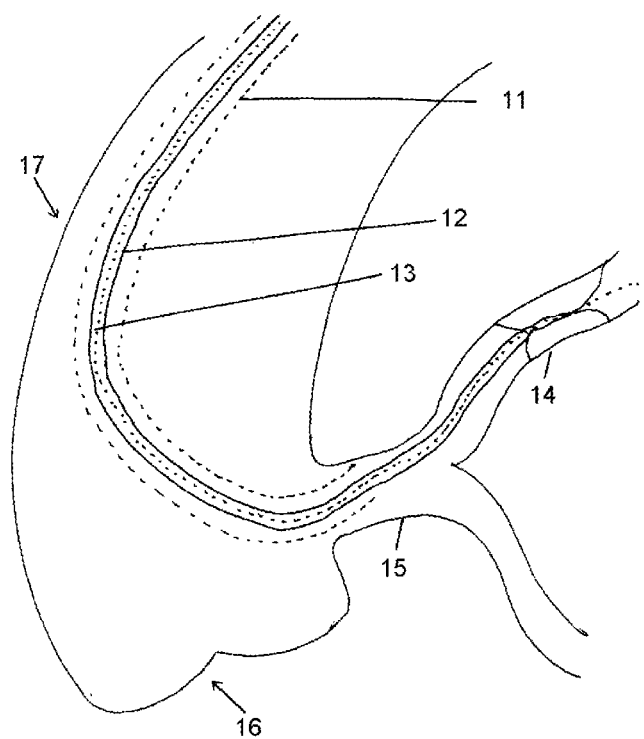
FIG. 1A illustrates a conventional catheter assembly showing an obstruction in the path of a balloon catheter.
Figure 1B:
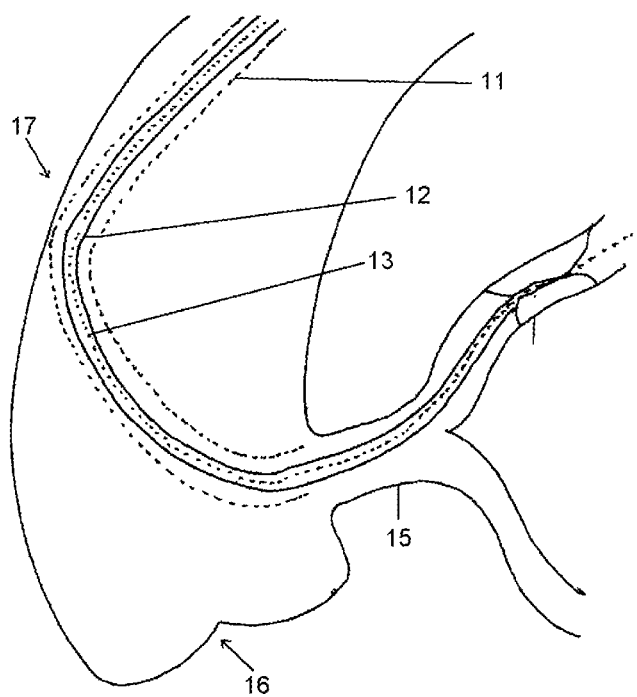
FIG. 1B illustrates another conventional catheter assembly showing the obstruction in the path of the balloon catheter.
Figure 1C:
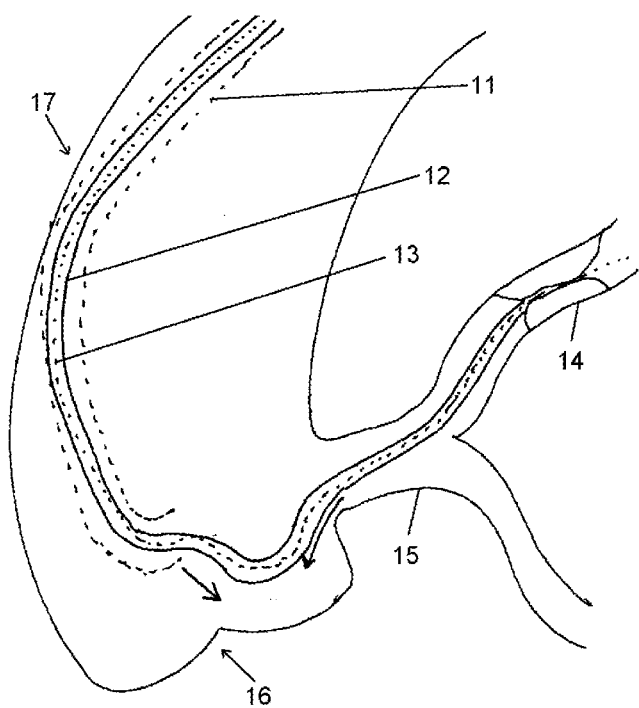
FIG. 1C illustrates another conventional catheter assembly showing the obstruction in the path of the balloon catheter.
Figure 1D:
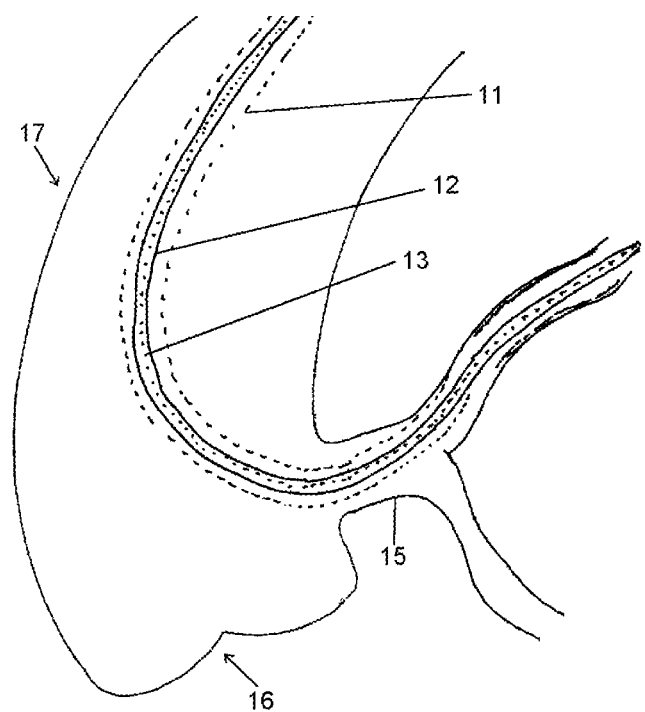
FIG. 1D illustrates another conventional catheter assembly showing sucking of the guide catheter up to the proximal in a situation when balloon got stuck in the lesion site.

FIGS. 1A to 1D illustrate a conventional guide catheter assembly showing an obstruction in the path of a balloon catheter and sucking of guide catheter (FIG. 1D). FIG. 1A depicts the conventional guide catheter assembly having a balloon catheter 12 and guide wire 13. A lesion 14 in the proximal left anterior descending (LAD) artery and the left main artery 15 in aota and the heart of patient is indicated in the FIG. 1A for illustration purposes.

Generally, a guide catheter 11 includes a proximal end P, a distal end D, and a lumen extending therethrough. A balloon catheter 12 is placed inside the guide catheter 11 having a proximal end, a distal end, a guide wire lumen and a balloon lumen. A fluid inflatable balloon is connected to the distal end of the balloon lumen. Guide wire 13 extends through the guide wire lumen of the balloon catheter. A drug eluting stent is mounted over the balloon for placing the same at a desired location in the artery (e.g., the LAD). The guide catheter assembly is inside the patient during the angioplasty procedure and in the proximity of aortic valve 16 and opposite aorta wall 17.

FIG. 1A clearly illustrates the start of the angioplasty procedure (either balloon alone or balloon and stent), first guide catheter 11 is inserted up to a certain distance, and thereafter guide wire 13 and balloon catheter 12 is inserted into the same. It is clear from the FIG. 1A that balloon catheter 12 reaches up to the lesion stage with the trajectory of guide wire 13.

However, when a lesion is present therein, lesion 14 prevents the balloon catheter from moving forward. As a result, in such circumstances, the doctor is required to push balloon catheter 12 with some additional force in order for the balloon catheter 12 tip to cross lesion 14 and the inflation of the balloon can take place at the desired location.

However, due to the presence of lesion 14, balloon catheter 12 is prevented from moving forward and its length in guide catheter 11, balloon catheter 12 and guide wire 13 assembly increases, and to accommodate this, the guide catheter is moved back.

FIG. 1B illustrates a situation where guide catheter 11 moves back and starts to collide with opposite aortic wall 17, which is not desired during an angioplasty procedure.

FIG. 1C illustrates that even if a continuous pushing force is applied, guide catheter 11 starts to move back and simultaneously balloon catheter 12 also starts to fall back towards the aortic valve 16 as shown by the direction arrows. In other words, it can be said that the length of balloon catheter 12 in guide catheter 11 increases. Additionally, in some instances, balloon catheter 12 is pulled and guide catheter 11 gets sucked in the proximal LAD as shown in FIG. 1D, which may result in injury.

Figure 2A:
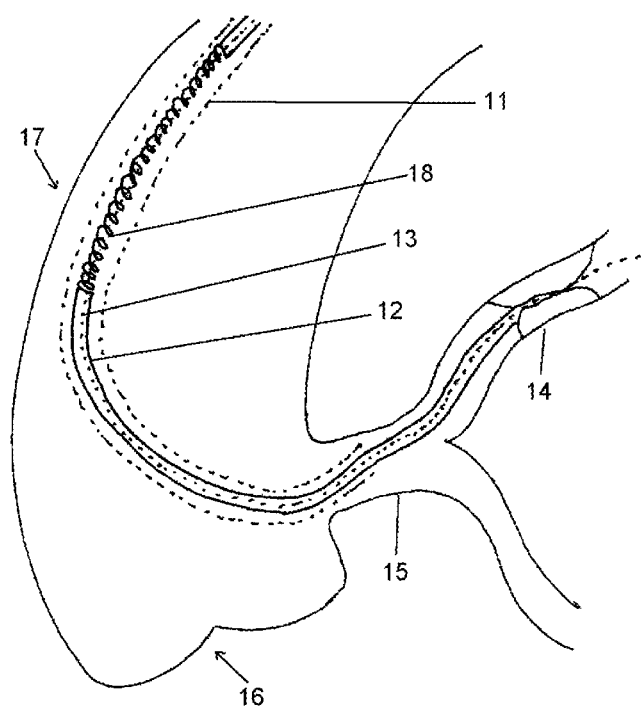
FIG. 2A illustrates a guide catheter device assembly, in accordance with an embodiment of the present invention.
Figure 2B:
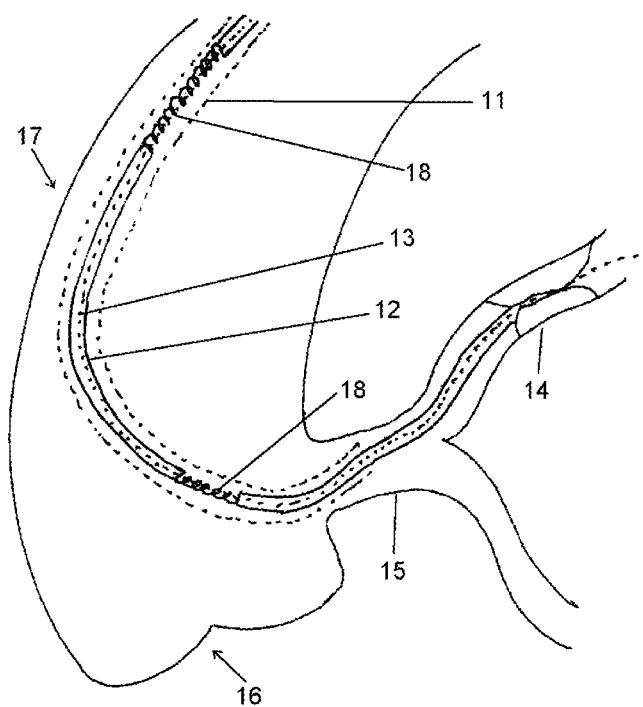
FIG. 2B illustrates a guide catheter device assembly, in accordance with an embodiment of the present invention.
Figure 2C:
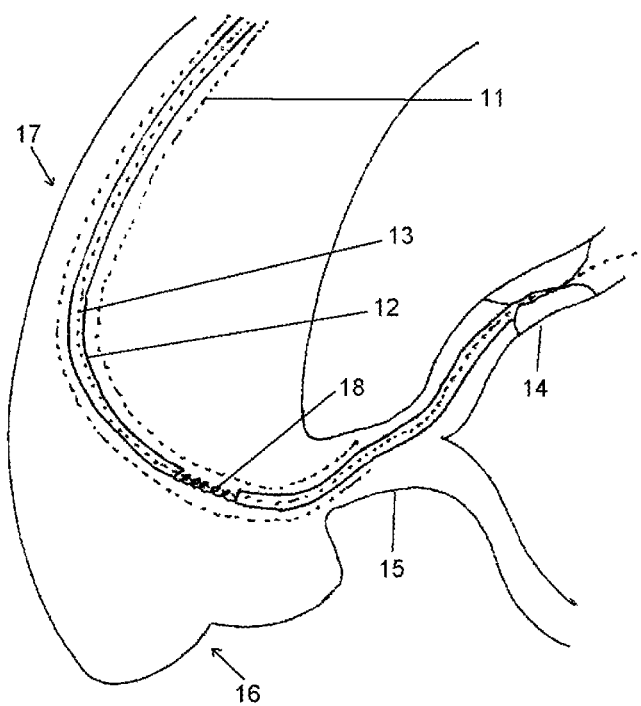
FIG. 2C illustrates a guide catheter device assembly, in accordance with an embodiment of the present invention.

FIGS. 2A-C illustrate a guide catheter device assembly, in accordance with an embodiment of the present invention. To overcome the above-mentioned problems in FIGS. 1A-1D, the guide catheter device assembly shown in FIGS. 2A-2C includes at least one resilient unit (e.g., a spring) 18 provided at a predetermined distance from the proximal end or the distal end of balloon catheter 12 for absorbing and transmitting a required force in order to maintain the alignment of guide catheter 11 and balloon catheter 12 as shown in FIG. 2A. In other words, balloon catheter 12 is provided with resilient unit 18 in some part thereof. In instances where a lesion 14 is present in the artery and the doctor exerts force to cross lesion 14, at least one resilient unit 18 is utilized for accurate placement of a balloon or a balloon and stent. Also, at least one resilient unit 18 is configured to absorb (as shown in FIG. 4B) the exerted force in order to maintain the alignment of guide catheter 11 and balloon catheter 12. If balloon catheter 12 is pushed further, the guide wire-balloon assembly will not start curving down and the guide wire 13 with the balloon will not fall back as shown in FIGS. 2A-2C, because of the additional force in the present situation, the spring is compressed and thereby the length of the balloon catheter is not increased, hence the problem of increase in the length of balloon catheter in the assembly is overcome. With said modification in the assembly, it should be appreciated that the balloon or the balloon with stent never comes out of the balloon, never causes embolisms somewhere in the vascular bed, and there is no shear injury to the vascular wall.

Figure 3:
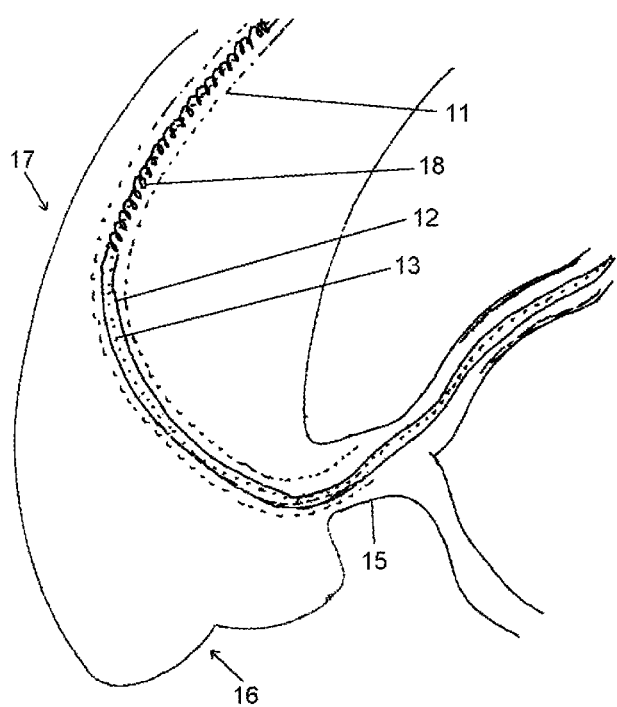
FIG. 3 illustrates a guide catheter device assembly showing stent deployment, in accordance with an embodiment of the present invention.

FIG. 3 illustrates a guide catheter device assembly, in accordance with an embodiment of the present invention. The guide catheter device assembly includes a guide catheter 11, a balloon catheter 12, a guide wire 13, and at least one resilient unit 18. In this embodiment, the guide catheter device assembly shows stent deployment.

Figure 4A:
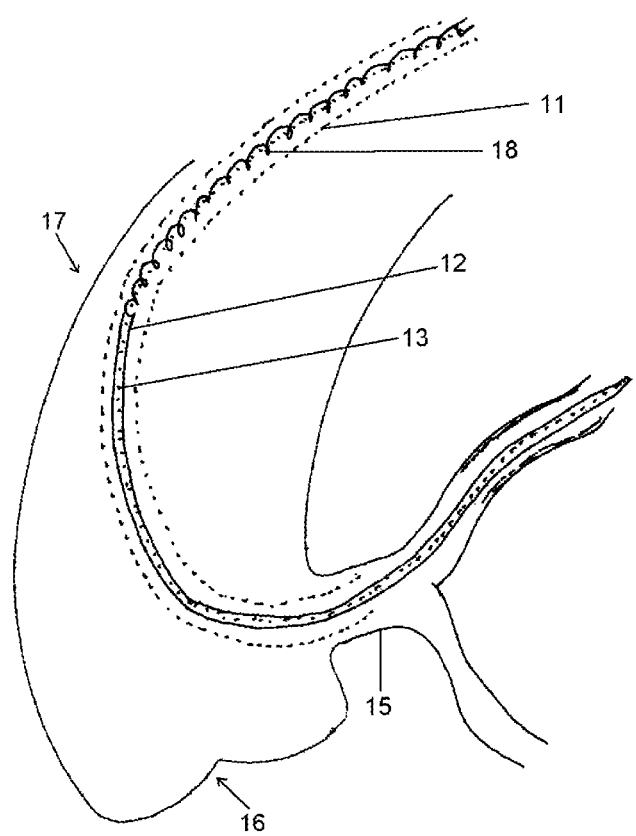
FIG. 4A illustrates a guide catheter device assembly showing elongation in the length of the spring in the assembly, in accordance with an embodiment of the present invention.
Figure 4B:
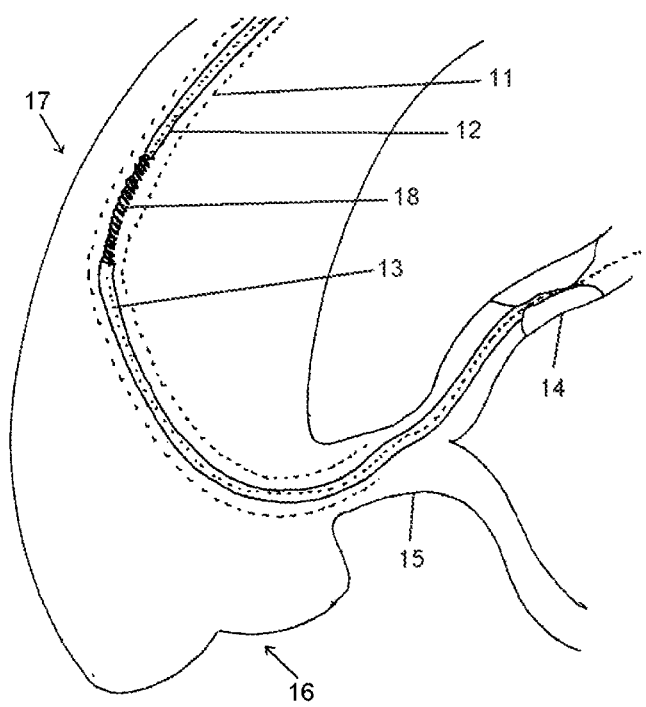
FIG. 4B illustrates a guide catheter device assembly showing compression in the length of the spring in the assembly, in accordance with an embodiment of the present invention.

FIG. 4A illustrates a balloon catheter device assembly, in accordance with an embodiment of the present invention. In this embodiment, the balloon catheter device assembly is shown with an increase in the length of at least one resilient unit 18.

FIG. 4B illustrates a guide catheter device assembly, in accordance with an embodiment of the present invention. In this embodiment, the guide catheter device assembly shown in FIG. 4B includes at least one resilient unit 18 in the assembly that is compressed.

Figure 5:
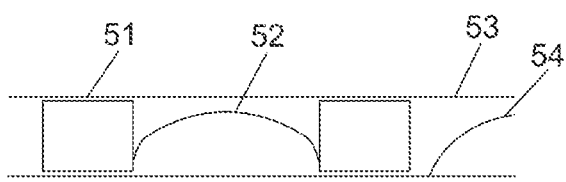
FIG. 5 illustrates a flat inner and outer surface of a stent, in accordance with an embodiment of the present invention.
Figure 6A:
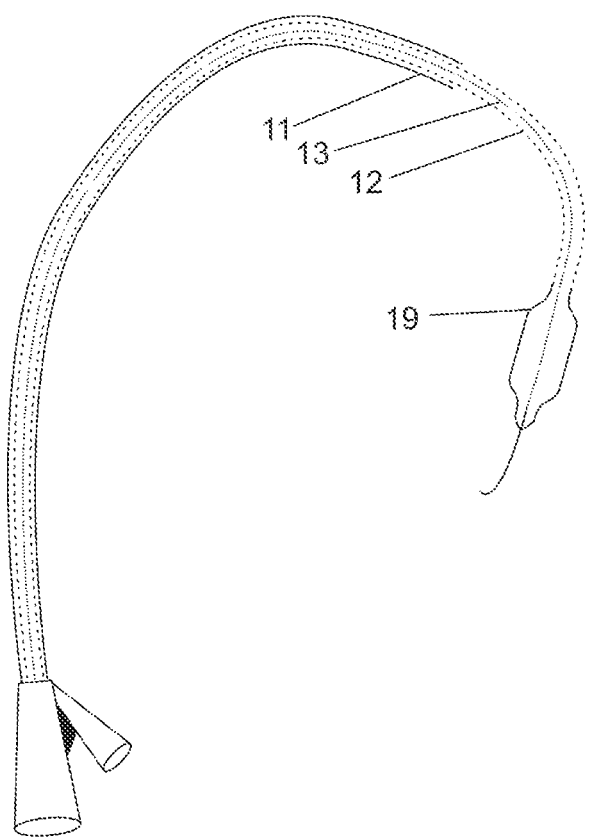
FIG. 6A illustrates a conventional catheter assembly.

FIG. 5 illustrates an inner and outer surface of a stent, in accordance with an embodiment of the present invention. In particular, FIG. 5 illustrates a flat inner and outer surface of stent 51, a heat expansible material 52 on the balloon, a compressive outer surface of stent 53, which does not allow heat expansible material 52 to cross the outer surface of stent 51, thereby keeping it in place. The compressive outer surface of stent 53 also does not allow an increase in the stent profile and balloon inner surface 54 such that heat expansible material 52 cannot disturb the lumen of the balloon FIG. 6A illustrates a conventional guide catheter assembly. In particular, FIG. 6A shows a guide catheter assembly having a guide catheter 11, a balloon catheter 12, a guide wire 13 and a balloon 19.

Figure 6B:
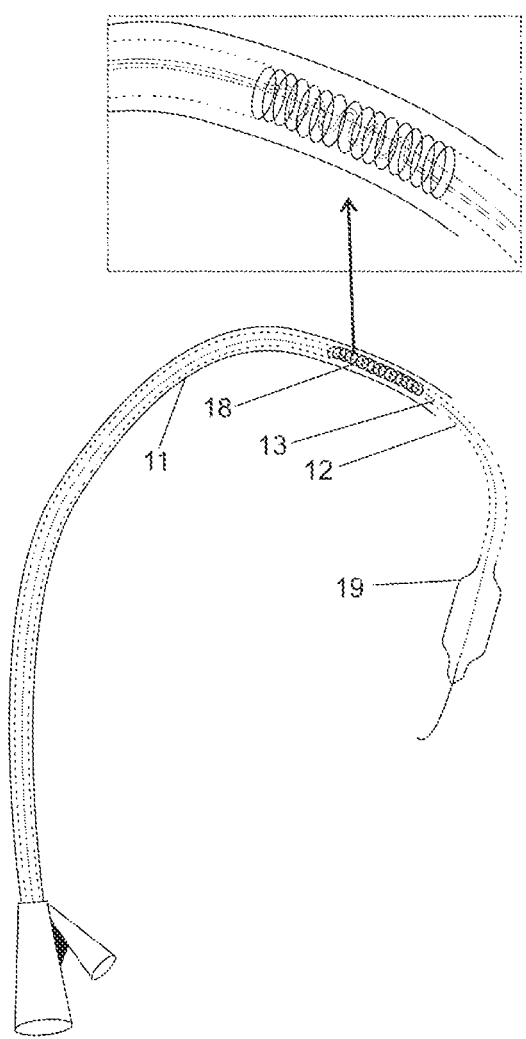
FIG. 6B illustrates a guide catheter assembly, in accordance with an embodiment of the present invention.
Figure 6C:
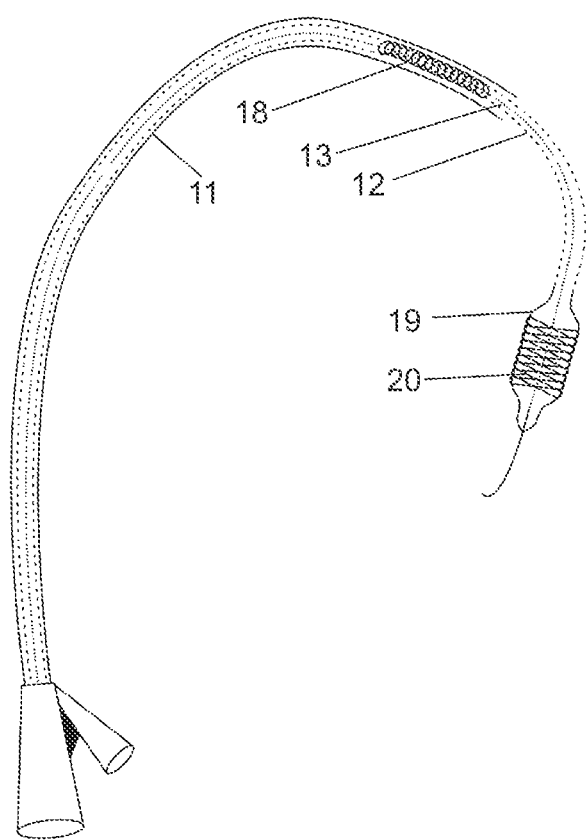
FIG. 6C illustrates a guide catheter assembly, in accordance with an embodiment of the present invention

FIG. 6B illustrates a guide catheter assembly, in accordance with an embodiment of the present invention. FIG. 6C also illustrates a guide catheter assembly in accordance with another embodiment of the present invention. Both FIGS. 6B and 6C illustrate a guide catheter 11, a balloon catheter 12, a guide wire 13, a resilient unit or spring 18 and a balloon 19 or a balloon with stent 20 as shown in FIG. 6C. In this embodiment, stent 20 is coated with a therapeutic agent composition. The therapeutic agent composition includes at least anticoagulants, a Platelet Glycoprotein IIb/IIIa Receptor blocker or antagonist, and a cytostasis or cytotoxic agent. It should be appreciated that the edges of the stent 20 include 3-30 a times higher concentration of drugs as compared to the middle segment of the stent in order to obtain a desired release profile of the coated composition.

It should be appreciated that the embodiments of the present invention are susceptible to various modifications and alternative forms, and specific embodiments thereof have been shown by way of example in the drawings and will be described in detail below. It should be understood, however, that the disclosure is not intended to limit the invention to the particular forms disclosed, but to the contrary, embodiments of the present invention cover all modifications, equivalents, and alternatives falling within the spirit and the scope of the invention as described herein and as defined by the appended claims.

It should be appreciated that one embodiment of the present invention resides in the therapeutic agent composition and the manner in which it is coated on the stent. Also, another embodiment of the present invention discloses an improved guide catheter assembly to implant the drug eluting stent safely.

The following paragraphs explain embodiments of the present invention with respect to a drug eluting stent and a guide catheter device assembly for implanting the same.

One embodiment of the present invention relates to a drug eluting stent for delivering therapeutic agents to a body lumen. The stent includes an expandable substrate configured for implantation in a vessel of a human body. The stent also includes a therapeutic agent composition coated over the stent. The therapeutic agent composition includes anticoagulants, a Platelet Glycoprotein IIb/IIIa Receptor blocker or antagonist, and a cytostasis or cytotoxic agent. The proportion of anticoagulants, the Platelet Glycoprotein IIb/IIIa Receptor blocker or antagonist, and the cytostasis or cytotoxic agent can be in the range of 1:0.15:0.5 to 1:0.2:1 in some embodiments, but may vary as would be appreciated by one of ordinary skill in the art. It should be appreciated that edges of the stent have a 3-30 times higher concentration of drugs as compared to the middle segment of the stent so as to obtain a desired release profile of the coated composition.

In another embodiment of the present invention, the anticoagulants are selected from the group consisting of heparin (unfractionated/fractionated), Xa inhibitors such as Fondaparinux, Idrabiotaparinux, Otamixaban, AVE5026, low molecular weight heparin such as enoxaparin, dalteparin, nadroparin, reviparin, ardeparin, certoparin, parnaparin, tinzaparin, and direct thrombin inhibitors such as lepirudin, argatroban, and bivalirudin, or a combination thereof.

In yet another embodiment of the present invention, the receptor blocker is selected from the group consisting of Glycoprotein IIb/IIIa inhibitors, (Platelet Glycoprotein IIb/IIIa Receptor blockers, platelet glycoprotein IIb/IIIa inhibitors or Platelet Glycoprotein IIb/IIIa Receptor Antagonists or Glycoprotein IIb/IIIa Antagonists) including drugs such as abciximab, tirofiban or eptifibatide, or a combination thereof.

In yet another embodiment of the present invention, a cytostasis or cytotoxic agent is selected from the group consisting of sirolimus, zotarolimus, tacrolimus, evrolimus, biolimus, merilimus, paclitaxel, or a combination thereof.

In yet another embodiment of the present invention, the stent has a zigzag pattern stent with a combination, or cocktail, of drug coatings.

In yet another embodiment of the present invention, the edges of the stent struts have a smooth outer surface.

In still another embodiment of the present invention, a guide catheter device is used for angioplasty. The device includes a guide catheter having a proximal end, a distal end, and a lumen extending therethrough. The device also includes a balloon catheter placed inside the guide catheter having a proximal end, a distal end, a guide wire lumen and a balloon lumen. The device further includes a fluid inflatable balloon connected to the distal end of the balloon lumen, and a guide wire extending through the guide wire lumen of the balloon catheter. A drug eluting stent included in the device can also be mounted over the balloon for placing the same at a desired location in the artery. The device includes at least one resilient unit provided at a predetermined distance from the proximal end of the balloon catheter for absorbing and transmitting a required force to maintain the alignment of the guide catheter and the balloon catheter. The edges of the stent have a higher concentration of drugs as compared to the middle segment of the stent.

In yet another embodiment of the present invention, the resilient unit is a spring.

In yet another embodiment of the present invention, the spring is circular, spiral-shaped, helical, or a combination thereof.

In yet another embodiment of the present invention, the stiffness of the spring is in the range 100 N/m to 5000N/m.

In yet another embodiment of the present invention, the spring is provided at any desired distance from the proximal end or the distal end, or both, preferably in the range of 5-25 centimeters (cm) from the proximal end of the balloon In yet another embodiment of the present invention, the balloon has a heat expansible material and a longer nose cone.

In yet another embodiment of the present invention, the stent has a zigzag pattern stent with a cocktail of drug coatings.

In yet another embodiment of the present invention, the spring comprises non-ferromagnetic material.

In yet another embodiment of the present invention, the resilient unit includes a spring of various lengths in the range of 0.5 cm to 20 cm.

In yet another embodiment of the present invention, the edges of the stent struts have a smoothened outer surface.

In yet another embodiment of the present invention, the strut length of the stent is in the range of 1-4 millimeters (mm).

In yet another embodiment of the present invention, the stent is coated with a composition of drugs that is selected from the group consisting of: anticoagulants such as heparin (unfractionated/fractionated), a Platelet Glycoprotein IIb/IIIa Receptor blocker or antagonist and a cytostasis or cytotoxic agent, wherein the proportion of anticoagulants, Platelet Glycoprotein receptor blocker or antagonist, and cytostasis or cytotoxic agent is in the range of 1:0.15:0.5 to 1:0.2:1.

In yet another embodiment of the present invention, the anticoagulants are selected from the group consisting of heparin (unfractionated/fractionated), Xa inhibitors such as Fondaparinux, Idrabiotaparinux, Otamixaban, AVE5026, low molecular weight heparin such as enoxaparin, dalteparin, nadroparin, reviparin, ardeparin, certoparin, parnaparin, tinzaparin, and direct thrombin inhibitors such as lepirudin, argatroban, and bivalirudin, or a combination thereof.

In yet another embodiment of the present invention, the receptor blocker is selected from the group consisting of Glycoprotein IIb/IIIa inhibitors, (platelet glycoprotein IIb/IIIa inhibitors or Platelet Glycoprotein IIb/IIIa Receptor Antagonists or Glycoprotein IIb/IIIa Antagonists) and includes drugs such as abciximab, tirofiban, eptifibatide, or a combination thereof.

In yet another embodiment of the present invention, the cytostasis or cytotoxic agent is selected from the group consisting of sirolimus, zotarolimus, tacrolimus, evrolimus, biolimus, merilimus, paclitaxel, or a combination thereof.

The following is a description of the therapeutic agent composition in accordance with one or more embodiments of the present invention. The stent is coated with a therapeutic agent composition that includes at least anticoagulants (first composition), a Platelet Glycoprotein IIb/IIIa Receptor blocker or antagonist (second composition), and a cytostasis or cytotoxic agent along with other pharmaceutically acceptable carriers (third composition). The first composition includes at least Heparin 100 IU, Eptifibatide 1000 micrograms, and Sirolimus 200 micrograms. The second composition includes enoxaparin, dalteparin, nadroparin, reviparin, ardeparin, certoparin, parnaparin, tinzaparin, bivalirudin, hirudin, argatroban, or a combination thereof, at 900 micrograms. The second composition also includes IIb/IIIa, abciximab, tirofiban, eptifibatide, or a combination thereof, at 650 micrograms, as well as Sirolimus, biolimus, merilimus, zotarolimus, tacrolimus, evrolimus, paclitaxel, or a combination thereof, at 175 micrograms. The third composition includes Enoxaparin, dalteparin, nadroparin, reviparin, ardeparin, certoparin, parnaparin, tinzaparin, bivalirudin, hirudin, argatroban, or a combination thereof, at 900 micrograms. The third composition includes IIb/IIIa, such as abciximab, tirofiban, eptifibatide, or a combination thereof, at 550 microgram, as well as sirolimus, biolimus, merilimus, zotarolimus, tacrolimus, evrolimus, paclitaxel, or a combination thereof, at 175 micrograms.

It should be appreciated that Heparin (unfractionated/low molecular) and receptor blockers can be released over a time period that ranges from 10 to 20 days. Further, the drug elutes a higher concentration in first 2-5 days and, thereafter, the drug releases slowly to prevent acute/sub-acute obstruction. Also, in this embodiment, the cytostasis/cytotoxic agent can be released from 10-90 days, depending on the agent and dose required to prevent restenosis.

Further, the aforementioned higher concentration of the composition can be coated on the ends at 5%, 10%, 15%, 20%, 25%, 30%, 35%, and 40% by weight, as compared to middle segment (completely or intermittently) of the stent in some embodiments. However, the precise amount used is subject to variation, as would be appreciated by one of ordinary skill in the art. It should be noted that if the concentration on the ends (proximal and distal ends) of the stent is higher than the middle segment by 10 to 30% by weight, the risk of restenosis and thrombosis can be mitigated. In another embodiment, the stent has an 18% higher concentration on the ends of any of the aforementioned compositions. This may provide improved results and eliminate the risk of restenosis and thrombosis. Because post PTCA restenosis can occur more often at the edges of the stent, the aforementioned experiments may be carried out in various concentrations. In addition, at the distal edge, the vessel may be tapered (the luminal diameter is less than the proximal edge of the stent) so there can be more relative barotrauma (injury to the vessel wall from pressure of the balloon and stent). Thus, higher drug doses at the edges may be useful for patients.

There are various critical positions for which a higher concentration of drugs is required, such as:
a) Ostial LAD, where the restenosis or stent thrombosis can affect the distal left main.
b) Ostial LCx proximal edge coming again in the distal left main.
c) Ostial D1(diagonal 1) affecting the proximal LAD.
d) Ostial OM1(obtuse marginal) affecting the proximal LCx.
e) Ostial PDA (posterior descending artery) affecting the main RCA bifurcation.

These examples show that proximal edge problems can be more problematic than the original disease itself (due to complications such as restenosis or stent thrombosis). Thus, proximal edge complications such as restenosis can be crucial. Therefore, higher doses of the drug at the two edges, especially the proximal edge (a higher drug dose at the edges than the main part, and the proximal edge dose that is higher than the distal edge dose) will be helpful to patients.

It should be further appreciated that the stent can be implanted at two critical places such as Ostial LAD and Ostial LCx, such that in the event of restenosis, the distal left main will be involved, which is a prone site to restenosis or stent thrombosis. As a result, a higher concentration of the coating of the composition can be provided at the proximal edge.

Described below is a guide catheter device assembly for implanting the stent, in accordance with one or more embodiments of the present invention.

The guide catheter device assembly can include a guide catheter, a balloon catheter and a guide wire, along with other attachments. Particularly, the device can include a guide catheter having a proximal end, a distal end, and a lumen extending therethrough. A balloon catheter is placed inside the guide catheter having a proximal end, a distal end, a guide wire lumen and a balloon lumen. A fluid inflatable balloon can be connected to the distal end of the balloon lumen and a guide wire can extend through the guide wire lumen of the balloon catheter. A drug eluting stent is mounted over the balloon for placing the balloon at a desired location in the artery. A resilient unit is provided at a predetermined distance from the proximal end of the balloon catheter for absorbing and transmitting a required force to maintain the alignment of the guide catheter and the balloon catheter. The edges of the stent have a higher concentration of drugs as compared to the middle segment of the stent.

The balloon catheter shaft can be modified by providing a resilient unit, such as a spring, at distance in the range of a ratio of 0.05 to 0.5 of the total length of the balloon catheter from the distal end. In the case of a rapid exchange type balloon catheter, a spring can be located at a distance in the range of a ratio of 0.05 to 0.5 from the distal end of the shaft or from the distal end of the transition tube. In the case of an obstruction, the spring can get compressed while pushing and absorbing the forward force and transmitting the force without disturbing the alignment, which is not possible in the conventional devices discussed above.

In the conventional device, in an ordinary balloon, pushing on the obstruction moves the guide wire and the guide catheter assembly back and causes them to fall back. Also, in the conventional device, if there is an obstruction in the path of the device, then a further push moves the guiding catheter back and the guide wire-balloon assembly will start to curve down, causing the guide wire with the balloon to fall back. The stent also occasionally comes off of the balloon and embolises somewhere in the vascular bed.

The following drawbacks are observed in various types of balloon catheter shafts, during the aforementioned pushing procedure. For instance, in a monorail type balloon (rapid exchange) system, if the wire is out prior to the spring, then sometimes the spring may buckle in the guide catheter. In another example, the guide wire can come out through the spring.

In some embodiments of the present invention, when force is applied to the balloon catheter during an angioplasty procedure upon encountering an obstruction in the artery, the spring can slowly get compressed in length due to the applied force and transmit the force forward. Further, the spring may remain in part of the balloon catheter, where the guide wire is inside the balloon catheter shaft and does not allow the direction to change. The balloon is placed in a manner that the above spring segment in the balloon catheter remains straight and the wire does not go through gaps of the spring.

It should be appreciated that the resilient unit described herein is a spring, but can be any other elastic mechanism that will be readily appreciated by a person of ordinary skill in the art.

In this embodiment, the resilient unit is an elastic object used to store mechanical energy. Springs are usually made from hardened steel. Small springs can be wound from pre-hardened stock, while larger springs can be made from annealed steel and hardened after fabrication. Some non-ferrous metals can also be used, including phosphor bronze and titanium for parts requiring corrosion resistance and beryllium copper for springs.

When a spring is compressed or stretched, the force it exerts is proportional to its change in length. The rate or spring constant of a spring is the change in the force it exerts divided by the change in the deflection of the spring. That is, it is the gradient of the force versus deflection curve. An extension or compression of the spring has units of force divided by distance, for example foot pounds per inch or N/m. The inverse of spring rate is compliance. The stiffness (or rate) of springs in parallel is additive, as is the compliance of springs in series.

Depending on the design and required operating environment, any material can be used to construct a spring, so long as the material has the required combination of rigidity and elasticity.

For the purpose of the embodiments of the present invention, springs can be classified depending on how the load force is applied to them: tension/extension spring, compression spring, or torsion spring. tension/extension springs are designed to operate with a tension load, so the spring stretches as the load is applied to it (pulling force applied). Compression springs are designed to operate with a compression load, so the spring gets shorter as the load is applied to it (pushing force is applied). Torsion springs, unlike the above springs in which the load is an axial force, has a torsion or twisting force, and the end of the spring rotates through an angle as the load is applied (pushing and rotation force is applied).

A helical spring, for example, is made of a coil or helix of wire. A coil spring or helical spring (made by winding a wire around a cylinder) and a conical spring are types of springs where the wire itself is twisted when the spring is compressed or stretched. These may be of two types: compression springs and tension, or extension, springs. Compression springs are designed to become shorter when loaded. The turns (loops) thereof are not touching in the unloaded position. Tension, or extension, springs are designed to become longer under load. The turns (loops) thereof are normally touching in the unloaded position.

In one or more embodiments of the present invention, the aforementioned springs are made of non-ferromagnetic material, which is pursuant to acceptable medical standards. The strength of the spring is sufficient to withstand the pushing force or pulling force and does not break and/or buckle in the balloon catheter. In other words, the spring does not undergo plastic strain or permanent deformation. The extension of springs can be described by Hooke's Law, where $F=-k*s$. This means: The force F required to extend or compress the spring depends in a linear manner on the range s by which one extends or compresses it. Derived from Hooke's law, a spring constant k is defined for various springs. It should be appreciated that the spring's stiffness (k) should preferably be in the range of 100N/m to 5000N/m, the pitch (distance between two adjacent strands) having a range of 0.1 mm to 3 mm, and the diameter of the spring should be in accordance with the size of balloon catheter, which is normally in the range of 0.5 mm to 16 mm. Further, the strands of the spring may be spiral, helical or oblique, or a combination thereof.

The following is a detailed description of the stent, in accordance with one or more embodiments of the present invention. Stent structure can be in a zigzag pattern, and have flat outer surface and/or a round/smooth outer surface, which does not cause injury to the patient after implantation. The outer surface texture can be created in such a manner that it can hold the therapeutic agent composition on its surface for a longer time (e.g., 5 to 20 days). The length of stent may vary in the range of 1-4.0 mm.

The following is a detailed description of the balloon or the balloon with stent, in accordance with one or more embodiments of the present invention. A balloon catheter can include at the distal end either a balloon or a balloon with a stent. In the case of a balloon with stent, the balloon is coated with heat expansible material on the outer surface, in part or in whole, and has a longer flexible nose cone (length is in the range 0.02-40 mm). The heat expansible material should not affect the lumen of the balloon. Also, the heat expansible material should not bind with the stent, and should not come off of the balloon.

Alternatively, a wire supplied with a receptacle at the distal segment allows attachment to the guide wire. The wire may be of two types of strength—for proximal lesions (the target lesion being close to the guiding catheter tip as proximal LAD) and distal lesions (the target lesion being distant to the guiding catheter tip as distal RCA). The stent segment can be short in length, may have a zigzag pattern for expansion and preventing shortening, may be a thin stent, may have a flat outer surface, and may have a larger zigzag segment window to allow side branch access. The outer surface of the balloon can have a small amount of heat expansible material to match the window on the stent. The balloon has a longer flexible nose (approximately 05-20 mms). The compressed balloon is heated and this material fits in the window (thus firmly gripping the stent when not deployed). The flat outer surface of the stent is in contact with the compressing surface so the heat-expansible material does not come over the compressing surface and entrap the stent. The heat expansible material does not come towards the inside of the balloon so as to affect its function. The heat expansible material does not bind with the stent material. The heat expansible material should not come off of the outer surface of the balloon. Since the heat expansible material is inside the compressing surface, the heat expansible material matches the outer diameter of the stent without increasing the profile of the mounted stent. When the balloon is expanded, the window enlarges and the stent is free from the heat expansible material. The stent can be coated with a therapeutic agent composition including heparin (unfractionated/low molecular), which can be released over 10 days. The maximum amount can be released in the first day and later more slowly to prevent acute/sub-acute obstruction.

The IIb/IIIa receptor blocker (as abciximab) can be released over 10 days with the largest amount in the first day, and later slowly to prevent acute/sub-acute obstruction.

A cytostasis/cytotoxic agent can also be released from 14-45 days depending upon the agent and dose to prevent restenosis.

Described below is the construction of a balloon catheter with a spring. There are various types of angioplasty balloon catheters available in the market, which are as follows:

1. Over-the-wire balloon catheter. An over-the-wire balloon catheter has two lumens: one for the guide wire and the other for balloon inflation. Both of the lumens run from the proximal edge to the distal edge of the catheter. However, it should be noted that such a catheter causes prolonged procedure time and more X-ray radiation dose.
2. Rapid exchange or monorail balloon catheter. The guide wire balloons exits the shaft or main body of the catheter at a predetermined distance (e.g., around 20-25 cm). This guide wire exit point is called the Rx port. The balloon lumen is connected to a stiff hypo tube, which runs up to the proximal end. The part between the Rx port and the distal end of the hypo tube is called the transition point.
3. Cutting balloon. A cutting balloon has blades to cut into atheroma in certain situations
4. Cutting wire balloon. A cutting wire balloon has wires at the balloon surface to help in cutting atheroma.
5. Probing balloon or fixed-wire balloon catheter. A probing balloon or fixed-wire balloon catheter has no wire port but, at the end, a steering guide wire is fixed, which is hardly used in the current perspective.
6. Perfusion balloon catheter. A perfusion ballooned catheter has an additional perfusion lumen to supply arterial blood in distal circulation while the balloon is inflated at low pressure.
7. Drug delivery balloon catheter. A drug delivery balloon catheter has a balloon surface that has a special modification for local drug delivery at a desired site in the artery.

The following description is for the construction of a balloon catheter according to one or more embodiments of the present invention. In this part of the specification, for illustration purposes, only the over-the-wire balloon catheter and the rapid exchange or monorail balloon catheter are modified and exemplified according to one or more embodiments of the present invention. However, similar modification can be extended to the other types of balloon catheters existing in the market.

EXAMPLE 1

Over-the-Wire Balloon Catheter (FIGS. 6B and 6C)

In a balloon catheter, there are two lumens, which normally run along the entire length of the balloon catheter (i.e. from the proximal end to the distal end). Particularly, one lumen is for inserting the guide wire and another lumen is for feeding the fluid for inflating or deflating the balloon during an angioplasty procedure. The length from the proximal end to the distal end is called the shaft, which can be made up of several materials such as nylon and high-density polyethylene, etc.

To modify the existing balloon catheter, a portion of the total length of the balloon catheter is provided with a resilient unit 18 such as spring. One end of the spring is connected with a proximal side of balloon catheter 12 and another end is connected to the distal end of balloon catheter 12 by any suitable technique, such as gas welding, pressure welding, etc. Particularly, the connection is made in such a manner that one lumen must remain inside the spring portion as shown in FIG. 6B (enlarged part of assembly).

Some portion of the second lumen (balloon lumen) is located inside the spring in a spiral form, enabling the adjustment of length concurrent to the spring action so as to avoid kinking/bending of the lumen.

Therefore, by providing at least one resilient unit (i.e. spring) 18 at a predetermined distance from the proximal end or the distal end of the balloon catheter 12 for absorbing and transmitting a required force so as to maintain the alignment of the guide catheter and balloon catheter as shown in FIG. 2A. In other words, the balloon catheter 12 is provided with a spring 18 in some part of the balloon catheter 12. When a lesion present in the artery and the doctor pushes to cross the lesion and for accurate placement of the balloon or balloon and stent, the resilient unit 18 absorbs (as shown in FIG. 4B) the pushing force, thereby maintaining the alignment of guide catheter 11 and balloon catheter 12. If the balloon catheter 12 is further pushed, the guide wire-balloon assembly will not start curving down and the guide wire with the balloon will not fall back as shown in FIGS. 2A to 2C. With the aforementioned modification in the assembly, it should be appreciated that the balloon or balloon with stent never comes out of the balloon and never causes embolisms somewhere in vascular bed, so there is no shear injury to the vascular wall.

EXAMPLE 2

Figure 7A:
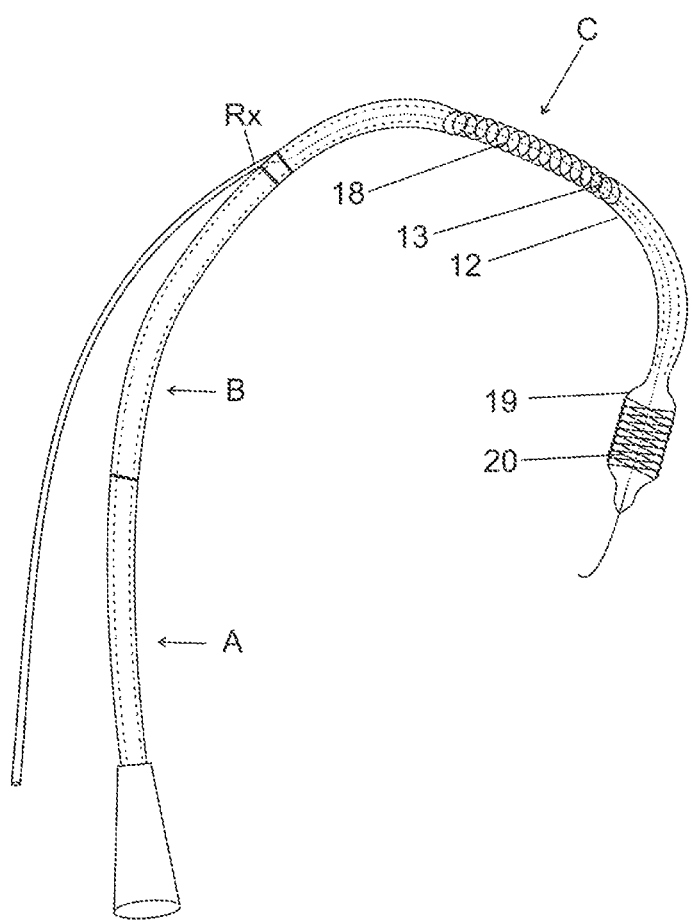
FIG. 7A illustrates a guide catheter assembly, in accordance with an embodiment of the present invention.
Figure 7B:
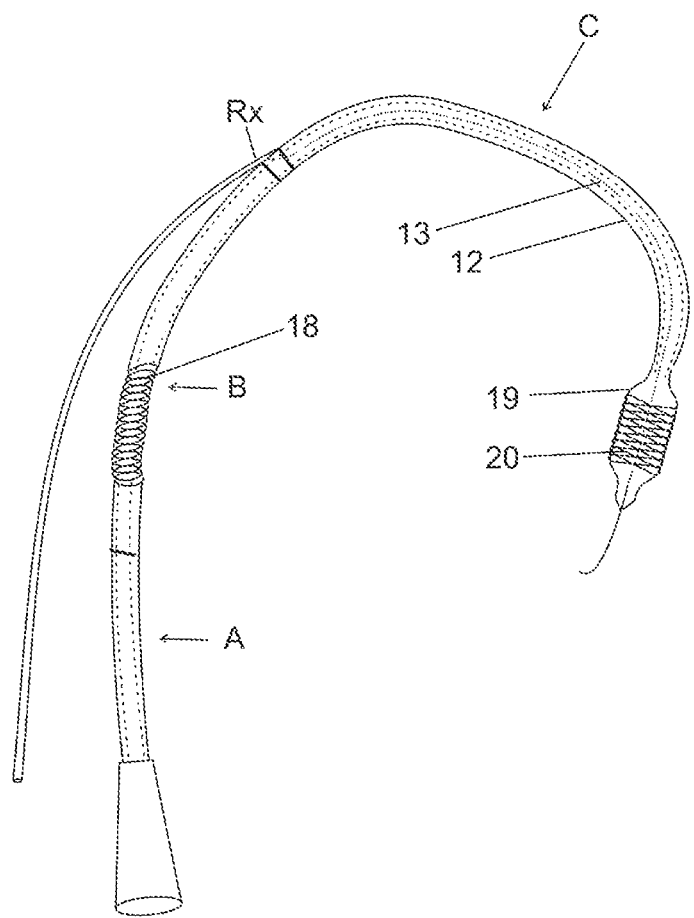
FIG. 7B illustrates a guide catheter assembly, in accordance with an embodiment of the present invention.

Rapid Exchange Balloon (FIGS. 7A and 7B)

FIGS. 7A and 7B illustrate a guide catheter assembly, in accordance with an embodiment of the present invention. The guide catheter assembly includes a guide catheter 11, a monorail or rapid exchange balloon catheter 12, a guide wire 13, a resilient unit or spring 18, and a balloon 19 or a balloon with stent 20. The balloon catheter 12 in case of rapid exchange can be construed in three parts, namely, a proximal tube (hypo tube) A, a transition tube B and a distal tube (shaft) C. At the junction of said transition tube B and distal tube C, a Rx port is provided to allow the guide wire 13 to enter into the balloon catheter 12 though the distal tube C. The fluid lumen is present inside the proximal tube A. The three parts of the balloon catheter 12 can be made of the same material or can be made of a different material.

To modify the existing balloon catheter, a portion of the transition tube B or the distal tube C, or both, is provided with a resilient unit 18 such as spring. In particular, the connection is made in such a manner that one lumen remains inside the spring portion.

During rapid exchange (FIGS. 7A and 7B), it can also be located in a way that the spring's 18 proximal end corresponds to the Rx port.

It should be appreciated that some portion of the second lumen (balloon lumen) is located inside the spring 18 in a spiral form, enabling the adjustment of length concurrent to the spring action so as to avoid kinking/bending of the lumen.

Because the spring 18 can absorb extra force during compression (high stiffness coefficient), the spring can be positioned in the transition zone (the part between the Rx port and the distal end of the hypo-tube). The spring 18 may not require guide wire 13 as it will not kink, thus the guide wire lumen is not an issue and the balloon fluid lumen can spiral inside or outside. For this type of catheter, the part of the hypo-tube outside the guiding catheter can be made up of thicker stainless steel so that it will not kink. For such a catheter, straight packing may be required and rather than curved standard packing By providing at least one resilient unit (e.g., spring) 18 at a predetermined distance from the proximal end or distal end of balloon catheter 12 for absorbing and transmitting a required force, the alignment of the guide catheter and the balloon catheter can be maintained as shown in FIG. 2A. In other words, the balloon catheter is provided with spring 18 in some part thereof. When a lesion is present in the artery and the doctor pushes to cross the lesion and for accurate placement of the balloon or balloon and stent, the resilient unit (or spring) 18 can absorb (as shown in FIG. 4B) the pushing force so as to maintain the alignment of the guide catheter and balloon catheter. If the balloon catheter 12 is further pushed, the guide wire-balloon assembly won't start curving down and the guide wire with balloon won't fall back as shown in FIGS. 2A to 2C. With the aforementioned modification in the assembly, it should be appreciated that the balloon or balloon with stent never comes out of the balloon and never causes embolisms somewhere in the vascular bed, and there is no shear injury to the vascular wall.

It should also be appreciated that above-mentioned modifications described in accordance with the embodiments of the present invention can be easily maneuvered by a person of ordinary skill in the art.

One or more embodiments of the present invention ensure ease in performing difficult cases including direct stenting. This will also help reduce incidence of acute/sub-acute obstruction and restenosis.

It should also be appreciated that the one or more embodiments of the present invention are applicable in cases of a peripheral balloon with/without stent.

In one or more embodiments the device includes a negligible and controlled jump, as in the case of rotablator use. As a result, clinical consequences are reduced or eliminated.

One having ordinary skill in the art will readily understand that the invention as discussed above may be practiced with steps in a different order, and/or with hardware elements in configurations that are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. A guide catheter device for angioplasty, comprising:
a guide catheter having a proximal end, a distal end, and lumen extending therethrough;
a balloon catheter placed inside the guide catheter, the balloon catheter having a proximal end, a distal end, a guide wire lumen and a balloon lumen;
a fluid inflatable balloon connected to the distal end of the balloon lumen;
a guide wire extending through the guide wire lumen of the balloon catheter; and
a drug eluting stent mounted over the balloon in order to place the same at a desired location in the artery;
wherein, the balloon catheter comprises at least one resilient unit provided at a predetermined distance from the proximal end of the balloon catheter, and is configured to absorb and transmit a required force to maintain the alignment of the guide catheter and the balloon catheter, the at least one resilient unit comprises a spring in a circular shape, spiral shape, helical shape, or a combination thereof; and
edges of the stent have a higher concentration of drugs as compared to a middle segment of the stent.

2. The guide catheter device according to claim 1, wherein the stiffness of the spring is in the range of 100 N/m to 5000 N/m.

3. The guide catheter device according to claim 1, wherein the spring is provided in the range of 5-25 cm from the proximal end of the balloon.

4. The guide catheter device according to claim 1, wherein the balloon has a heat expansible material and an extended nose cone.

5. The guide catheter device according to claim 1, wherein the stent comprises a zigzag pattern stent with a cocktail of drug coatings.

6. The guide catheter device according to claim 1, wherein the spring comprises non-ferromagnetic material.

7. The guide catheter device according to claim 1, wherein the resilient unit comprises a spring ranging from 0.5 cm to 20 cm.

8. The guide catheter device according to claim 1, wherein the edges of the stent struts comprise a smoothened outer surface.

9. The guide catheter device according to claim 1, wherein strut length of the stent ranges from 1 mm to 4 mm.

10. The guide catheter device according to claim 1, wherein the stent is coated with a composition of drugs comprises:
a) anticoagulants,
b) a Platelet Glycoprotein IIb/IIIa Receptor blocker or antagonist, and
c) a cytostasis or cytotoxic agent,
wherein, the proportion of the anticoagulants, platelet glycoprotein IIb/IIIa receptor blocker or antagonist, and the cytostatis or cytotoxic agent is in the range of 1:0.15:0.5 to 1:0.2:1.

11. The guide catheter device according to claim 10, wherein the anticoagulants are selected from the qroup consisting of heparin (unfractionated/fractionated), Xa inhibitors such as Fondaparinux, ldrabiotaparinux, Otamixaban, AVE5026, low molecular weight heparin such as enoxaparin, dalteparin, nadroparin, reviparin, ardeparin, certoparin, parnaparin, tinzaparin, and direct thrombin inhibitors such as lepirudin, arqatroban, and bivalirudin, or a combination thereof.

12. The guide catheter device according to claim 10, wherein the receptor blocker is selected from the group consisting of Glycoprotein IIb/IIIa inhibitors, platelet glycoprotein IIb/IIIa inhibitors, Platelet Glycoprotein IIb/IIIa Receptor Antagonists, or Glycoprotein IIb/IIIa Antagonists), and the receptor blocker comprises abciximab, tirofiban, eptifibatide, or a combination thereof.

13. The guide catheter device according to claim 10, wherein the cytostasis or cytotoxic agent is selected from the group consisting of sirolimus, zotarolimus, tacrolimus, evrolimus, biolimus, merilimus, paclitaxel, or a combination thereof.

* * * * *